United States Patent [19]

Ng et al.

[11] Patent Number: 5,030,457
[45] Date of Patent: Jul. 9, 1991

[54] BIOERODIBLE POLYMERS USEFUL FOR THE CONTROLLED RELEASE OF THERAPEUTIC AGENTS

[75] Inventors: Steve Y. W. Ng, San Francisco; Jorge Heller, Woodside, both of Calif.

[73] Assignee: Pharmaceutical Delivery Systems, Inc., Menlo Park, Calif.

[21] Appl. No.: 400,532

[22] Filed: Aug. 28, 1989

[51] Int. Cl.$^5$ .................... C08G 65/34; A61K 9/14
[52] U.S. Cl. ................................ 424/486; 424/423; 424/457; 514/179; 528/425
[58] Field of Search ............... 528/425; 424/423, 486, 424/457; 514/179

[56] References Cited

U.S. PATENT DOCUMENTS

| | | | |
|---|---|---|---|
| 4,066,747 | 1/1978 | Capozza | 528/425 X |
| 4,079,038 | 3/1978 | Choi et al. | 528/425 X |
| 4,119,579 | 10/1978 | Capozza | 528/425 X |
| 4,304,767 | 12/1981 | Heller et al. | |
| 4,405,798 | 9/1983 | Hall et al. | |
| 4,549,010 | 10/1985 | Sparer et al. | 528/425 X |

OTHER PUBLICATIONS

Burt, et al., *J. Amer. Chem. Soc.* (1982) 104:3687-3690.
Padias, et al., *Macromolecules* (1982) 15(2):217-223.
Padias, et al., "Synthesis and Polymerization of Atom-Bridged Bicyclic Acetals and Orthoesters: A New Mechanism," pp. 258-259.
Padias, et al., "Ring-Opening Polymerization," Chapter 23, pp. 314-333, ACS Symposium Series 286, American Chem. Soc., Washington, D.C. (1985).
Szymanski, et al., *J. Polymer Science: Polymer Letters Edition* (1983) 21:177-187.

*Primary Examiner*—Earl Nielsen
*Attorney, Agent, or Firm*—Dianne E. Reed

[57] ABSTRACT

Bioerodible ortho ester polymers useful for preparing soft form bioerodible pharmaceutical compositions such as ointments, creams, gels and the like are provided. A novel synthetic method for preparing the polymers is provided as well. Synthesis involves a one-step reaction between a monomeric ortho ester and a triol. The pharmaceutical compositions of the invention are useful for the controlled release of therapeutic agents, and may be administered for a variety of purposes, such as for the treatment of deep wounds, including burns, and for the treatment of periodontal disease.

26 Claims, 1 Drawing Sheet

BIOERODIBLE POLYMERS USEFUL FOR THE CONTROLLED RELEASE OF THERAPEUTIC AGENTS

TECHNICAL FIELD

The present invention is in the fields of polymer chemistry and drug delivery. It concerns certain ortho ester polymers and methods for their preparation. These materials are bioerodible polymers, i.e., polymers containing hydrolytically labile linkages which undergo cleavage at physiologic conditions. These bioerodible polymers are useful for the controlled release of therapeutic agents. Thus the invention relates to soft drug dosage forms such as bioerodible ointments, gels, creams and the like formulated with these ortho ester polymers, and to the use of these soft bioerodible dosage forms in the treatment of disease conditions such as deep wounds, periodontal disease, and the like.

BACKGROUND OF THE INVENTION

Bioerodible polymers used to control the release of therapeutic agents physically dispersed in the polymer matrix have been described in a variety of contexts. One matrix which has been successful is a family of poly(ortho esters). These materials contain the pH-sensitive ortho ester linkage in their polymer backbone. Such polymers are described, for example, in U.S. Pat. No. 4,304,767 to Heller et al. Because the ortho ester linkages within these polymers are relatively stable at neutral pH, and hydrolyze progressively faster with the decreasing pH of the surrounding medium, the rate of erosion of the polymer can be manipulated within a very wide range by incorporating various levels and strengths of acidic excipients into the polymer matrix.

The method of preparing polymers according to the aforementioned patent comprises the addition of polyols to diketene acetals as shown in Scheme 1.

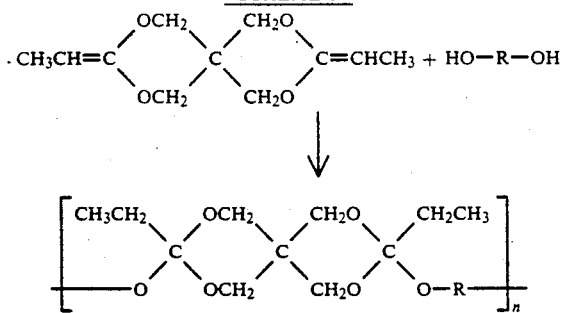

Using this scheme, almost any diketene acetal and any diol can be used, and the synthetic method is thus extremely versatile. Polymers synthesized by this method are, however, not optimal for preparing soft or amorphous drug dosage forms such as bioerodible ointments, creams or gels due to the relatively rigid pentaerythritol segment in the polymer backbone.

There is a need in the art for a bioerodible composition which has a molecular structure of sufficient flexibility to enable its use as a bioerodible matrix in soft dosage forms such as ointments, gels, creams, or the like. An ideal material would enable the topical delivery of an effective dose level of pharmaceutical agent from an ointment or the like at a desired rate for a period of time dictated only by clinical considerations and not by limitations of the ointment cream or gel formulation. The ability to achieve this is particularly important with antibacterial agents such as 4-homosulfanilamide, since excessive and uncontrolled application of the drug can produce serious side effects, e.g., acid-base disturbances associated with carbonic anhydrase inhibition. The present invention provides bioerodible ointments, gels, creams, etc., from which the release rate of the drug to be delivered—as well as the desired time period for drug delivery—can be carefully controlled. It provides materials which bioerode to small, water-soluble molecules that leave no residues in the tissue of the patient undergoing treatment. This opens the door for improved treatment of burns, wounds, especially deep wounds, and like applications by the controlled delivery of drugs over prolonged periods of time.

SUMMARY OF THE INVENTION

It is accordingly a primary object of the present invention to address the aforementioned needs in the art, and to provide bioerodible compositions useful in soft dosage form for the controlled release of therapeutic agents.

It is another object of the invention to provide these bioerodible compositions in the form of bioerodible ointments, gels, creams or the like.

It is another object of the invention to provide a novel method of synthesizing certain bioerodible ortho ester polymers useful for such compositions, as well as certain novel bioerodible ortho ester polymers themselves.

It is a further object of the invention to provide a bioerodible ointment and method for the treatment of deep wounds.

These objects are achieved by the present invention. In accord with this invention, a method is provided for synthesizing a bioerodible ortho ester polymer. This method involves:

reacting a monomeric ortho ester having the general formula

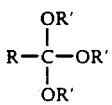

wherein R is hydrogen or an alkyl of 1 to 10 carbon atoms and R' is a lower alkyl of 1 to 6 carbon atoms, with a triol having the general formula

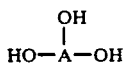

wherein A is alkylene or cycloalkylene of at least 5 carbon atoms, or an oxyalkylene of at least 5 carbons and having its oxygen as an ether linkage, e.g., within a saccharide structure. This reaction forms an ortho ester polymer containing a mer unit having the following general formula (I)

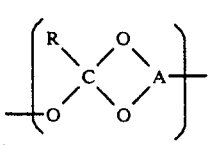

wherein the A and R units are as just described. This ortho ester polymer is another aspect of this invention.

In another aspect of the invention, bioerodible pharmaceutical compositions are provided based on these ortho ester polymers. These compositions are in ointment, gel, cream, or similar soft dosage form and contain one or more of these bioerodible ortho ester polymers with an effective amount of a therapeutic agent useful for a selected therapeutic purpose dispersed therein. This aspect of the invention also relates to a method for the prolonged treatment of disease states in man and animals such as treating burns, deep wounds, and the like. This method comprises administering topically to such a patient a pharmaceutical ointment, gel, cream, or the like, of this invention and thus achieving controlled bioerosion of the ortho ester polymer and the gradual exposure and controlled delivery of the therapeutic agent.

BRIEF DESCRIPTION OF THE INVENTION

FIG. 1 is a graph illustrating the effect of an acidic excipient on the rate of bioerosion of the ortho-ester-based compositions of this invention.

DETAILED DESCRIPTION OF THE INVENTION

A. Definitions

Figure 1:
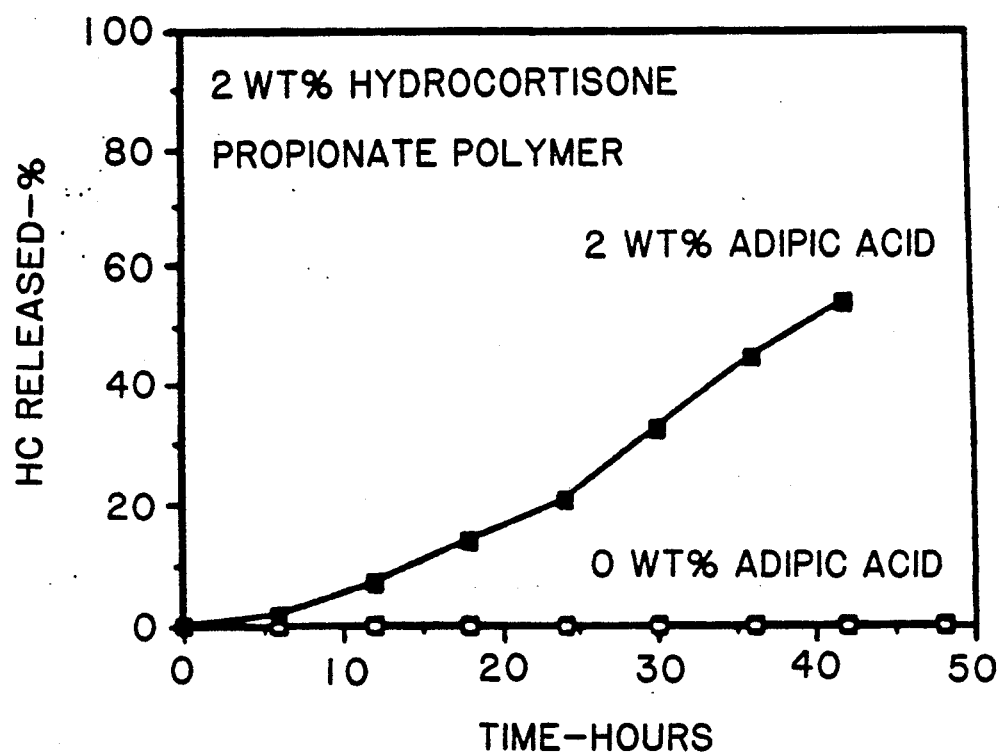

The term "mer" is used to mean the structurally recurring units or monomer units of the ortho ester polymers provided by the present invention. The mer units of any given polymer may be the same or different; when different, they may be arranged in block or random fashion. When all the mer units of a polymer are the same, the polymer is called a homopolymer. When there are 2 or more mer units in a polymer, the polymer is called a copolymer. The present invention involves both homopolymers and copolymers.

The term "bioerodible" as used herein to describe the polymers of the present invention is synonymous with the term of art "biodegradable." These terms denote the property of a body of solid gel polymer to undergo degradation, erosion and solubilization as a result of hydrolysis of labile linkages at the physiologic conditions of use.

The terms "therapeutic agent" or "drug" are used interchangeably to mean a compound or composition of matter which, when administered to an organism (human or animal) induces a desired pharmacologic and/or physiologic effect by local and/or systemic action. In general, the terms include the therapeutic or prophylactic agents in all major therapeutic/prophylactic areas of medicine.

The term "effective amount" as used herein intends that quantity of a therapeutic agent that, when administered to a patient, is required to provide the desired or intended beneficial effect without intolerable side effects, such as toxicity. When used in the context of controlled delivery or prolonged delivery of drug, the term can include a temporal aspect--noting that the rate of administration gives the desired effect without intolerable side effects.

The term "lower alkyl" is intended to mean linear, branched or cyclic alkyl moieties having 1 to 6, and more typically 1-5 carbon atoms, inclusive.

The terms "alkylene" and "cycloalkylene" have their usual meaning defining aliphatic linking groups, preferably aliphatic hydrocarbon groups which serve as a bridge between 2 or more other groups.

The term "oxyalkylene" defines an aliphatic linking group containing 1 or more ether oxygens and providing 2 or more carbons as bridge points to other groups. Oxyalkylene groups can be linear, branched or cyclic.

B. Synthetic Method

In the synthesis aspects of the present invention, a method is provided for synthesizing certain bioerodible ortho ester polymers. The synthesis is a simple, straightforward reaction which may be accomplished in one step in a single reaction vessel. The synthesis involves the reaction of a monomeric ortho ester having the general formula

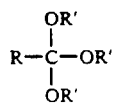

wherein R is a hydrogen or an alkyl of 1 to 10 carbon atoms and each of the Rs is independently selected from lower alkyls, with a triol having the general formula

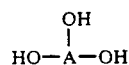

In this triol, A is an alkylene or a cycloalkylene moiety of 5 carbon atoms or more, or is an oxyalkylene. If cycloalkylene or a cyclic oxyalkylene, A will preferably contain 1 to 3, more preferably 1 or 2, rings. The reaction is carried out to form an ortho ester polymer which comprises mer units of the structure (I)

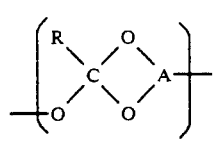

In preferred embodiments, the R moiety of the monomeric ortho ester reactant is a lower alkyl, and the R' moieties are the same alkyl, either methyl or ethyl. In preferred embodiments, the triol reactant, the A moiety, is either alkylene or cycloalkylene or oxyalkylene of 5 carbon atoms or more, preferably 5 to 20 carbon atoms, and more preferably 5 to 10 carbon atoms. It is preferred that 2 of the hydroxyl groups of the triol be separated by either 2 or 3 carbon atoms (i.e., so that x in the below structures is 0 or 1, respectively), to enable ring formation during polymerization, while the third hydroxyl group is preferably separated from the closer of the first 2 hydroxyl groups by 3 carbon atoms or more, (i.e., so that in the below structures y is greater than or equal to 2). This spacing of the third hydroxyl unit will prevent interference with the ring-forming reaction. Thus, in one group of preferred triols, A is a linear alkylene moiety, i.e., having the structure

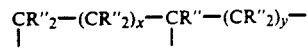

so that the triol has the structure

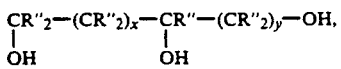

in which the various R" groups are independently selected from the group consisting of hydrogen and lower alkyls, x is 0 or 1, and y is greater than or equal to 2. If A is cycloalkylene, the ring structure preferably is such as to give this preferred hydroxyl spacing and facilitate ring closure. If oxyalkylene, A may be a cyclic sugar residue in which 2 of the triol hydroxyl moieties are α,β-cis so as to facilitate ring formation, while the other, third hydroxyl moiety is trans to the first 2 hydroxyl groups and separated therefrom by 3 or more carbon atoms, typically located in the 5'-position of a pentafuranose ring as in the structure:

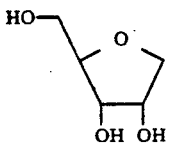

Compounds containing analogous substituted pentafuranose rings are within the purview of the present invention as well.

The synthesis reaction of the ortho ester monomer and triol is carried out either neat or in an aprotic solvent such as tetrahydrofuran (THF), cyclohexane, ethylene glycol dimethyl ether (glyme), diglyme, cymene, cumene, chlorinated hydrocarbons, or the like. More typically, solvent is present. Typical concentrations of the two reactants can range from essentially 100% (neat) down through about 10% by weight or lower, when solvent is used. In either case, care must be taken to maintain anhydrous conditions. The reaction can be carried out at reflux and thus, depending upon the solvent, at temperatures in the range of 50°–150° C., preferably 50°–90° C. The approximate molar ratio of reactants set at about 1:1 if it is desired to maximize the molecular weight of the polymer, but can be varied if a lower molecular weight polymer is desired (e.g., to make a less viscous ointment). It is typically preferred to carry out the reaction in the presence of an acid catalyst, although in cases where the reactants are acidic, a catalyst is unnecessary. Examples of suitable acid catalysts include p-toluenesulfonic acid and methanesulfonic acid. The amount of acid catalyst can range from 0% (based on its optional presence) to about 1% molar (based on the amount of triol present).

C. Novel Polymers

The novel ortho ester polymers provided by the present invention preferably contain mer units represented by Formula (I) wherein

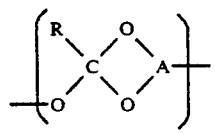

R is hydrogen or an alkyl of 1 to 10 carbon atoms, preferably a lower alkyl; and A is a cycloalkylene of at least 5 carbon atoms, a cyclooxyalkylene of at least 5 carbon atoms (as in the pentafuranose ring illustrated above), or a linear or branched alkylene moiety of at least 5 carbon atoms given by the structure

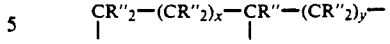

In this latter structure, the R" moieties are independently selected from the group consisting of hydrogen and the lower alkyls, x is 0 or 1, and y is an integer greater than or equal to 3.

Typically, although not necessarily, the polymers have molecular weights of at least about 5,000, more preferably at least about 20,000, and most preferably at least about 50,000, and the number of repeating mer units in the polymer will normally be in the range of 2 to 1000, preferably 2 to 200, and most preferably 5 to 200.

These polymers have the desirable properties of being able to undergo bioerosion and of being less rigid and more flexible and conforming than prior ortho ester polymers.

C. Pharmaceutical Compositions

The pharmaceutical compositions of this invention comprise a selected therapeutic agent or number of agents dispersed in a novel bioerodible ortho ester polymer as described in the preceding section. While the preferred pharmaceutical compositions of the invention are bioerodible ointments, gels, creams, and similar soft dosage forms adapted for the topical or parenteral administration of therapeutic agents, other modes of administration (e.g., transdermal) and compositional forms (e.g., more rigid transdermal forms) are within the scope of the invention as well.

The bioerodible ointments, gels and creams of the invention will include: an ointment, gel or cream base comprising one or more of the bioerodible ortho ester polymers described herein and a selected therapeutic agent. The therapeutic against, whether present as a liquid, a finely divided solid, or any other physical form, is dispersed in the ointment, gel or cream base. Typically, but optionally, the compositions include one or more other components, e.g., nontoxic auxiliary substances such as colorants, diluents, odorants, carriers, excipients, stabilizers or the like.

The amount of active agent will be dependent upon the particular drug employed and condition being treated. Typically the amount of drug represents about 0.001% to about 70%, more typically about 0.001% to about 50%, most typically about 0.001% to about 20% by weight of the total composition being common.

The quantity and type of ortho ester polymer incorporated into the ointment, gel, cream, etc., is variable. For a more viscous composition, a higher molecular weight polymer is used. If a less viscous composition is desired, a lower molecular weight polymer can be employed, i.e., one which is prepared with other than a 1:1 reactant ratio. The product may be based on only one polymer or it may comprise a mixture of polymers.

While not essential for topical or transdermal administration of many drugs, it may in some cases, with some drugs, be preferred that a skin permeation enhancer be coadministered therewith. Any number of the many skin permeation enhancers known in the art may be used. Examples of suitable enhancers include dimethylsulfoxide (DMSO), dimethylformamide (DMF), N, N-dimethylacetemide (DMA), desylmethylsulfoxide ($C_{10}MSO$), ethanol, eucalyptol, lecithin, and the 1-N-dodecylcyclazacycloheptan-2-ones (available under the trademark Azone ® from the Nelson Research and Development Company, Irvine, California).

It is additionally preferred to incorporate an acidic excipient into the bioerodible dosage form in order to control the rate of polymer bioerosion. The ortho ester linkages of the bioerodible polymers are relatively stable at basic or neutral pH and are hydrolized at progressively increasing rates as the pH of the medium surrounding the polymer decreases. Thus, hydrolytic lability and the rate of erosion and drug release can be increased by incorporation of one or more acidic components. Preferred acidic excipients are aliphatic acids, typically present at 0-10 wt %, more preferably 1-5 wt %, of the bioerodible composition. Solid but water soluble aliphatic acids are generally favored. Examples of acidic excipients useful in conjunction with the present invention include adipic, citric, suberic, maleic and itaconic acids. Basic excipients may also be used to slow the rate of release.

The variety of different therapeutic agents which can be used in conjunction with the bioerodible compositions of the invention is vast. In general, therapeutic agents which may be administered via the pharmaceutical compositions of the invention include, without limitation: antiinfectives such as antibiotics and antiviral agents; analgesics and analgesic combinations; anorexics; antihelminthics; antiarthritics; antiasthmatic agents; anticonvulsants; antidepressants; antidiabetic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers.

In two particularly preferred embodiments the therapeutic agents for administration in conjunction with the bioerodible polymers of the invention are antibacterial agents for the treatment of deep wounds, and antibiotics for periodontal treatment (e.g., tetracycline or the like). Other preferred drugs for use with the presently disclosed polymers include proteinaceous drugs such as epidermal growth factors or growth hormones.

D. Administration and Use

Depending on dosage form, the pharmaceutical compositions of the preceding section may be administered in different ways, i.e., topically, parenterally, or the like. Preferred dosage forms are soft dosage forms which can be applied directly to the afflicted tissue for the topical delivery of drug contained within an ointment, gel or cream. The ortho ester polymer, upon contact with body fluids including perspiration, saliva, or the like (depending upon the mode of administration), undergoes gradual bioerosion with concomitant gradual exposure of the dispersed drug to the afflicted tissue. This can result in prolonged delivery (over, say, 1 to 10,000 hours, preferably 2 to 1000 hours) of effective amounts (say, 0.0001 mg/kg/hour to 10 mg/kg/hour) of the drug. This topical application can be repeated as necessary depending on the subject being treated, the severity of the affliction, the judgment of the prescribing physician, and the like. Topical application can be enhanced by occlusion, i.e., placing a barrier over the area treated so as to enhance absorption into the skin. Topical administration is preferred for wound healing and in the treatment of periodontal disease.

Parenteral administration of a bioerodible composition of the invention can be effected by either subcutaneous or intramuscular injection. The bioerodible ointment, gel or cream may be injected as is or in combination with one or more auxiliary components as described above. Parenteral delivery is preferred for administration of proteinaceous drugs such as growth factors, growth hormone, or the like.

EXAMPLES

The examples presented below are provided as a further guide to the practitioner of ordinary skill in the art, and are not to be construed as limiting the invention in any way.

EXAMPLE 1

Under anhydrous conditions, 48.669 g (0.30 moles) of triethylorthoacetate, 40.25 g (0.30 moles) of 1,2,6-hexanetriol and 20 mg of p-toluenesulfonic acid were weighed into a 500 ml round bottom flask equipped with a magnetic stirring bar. To the flask was added 300 ml cyclohexane and the flask was adapted to a 60 cm spinning band column. The reaction flask was heated at 100° C. with vigorous stirring and the distillate, which included an azeotrope of by-product and cyclohexane ethanol, was removed rapidly at 65° C. while a strictly anhydrous condition was maintained. As the boiling point started to climb beyond 65° C., the distillation rate was reduced to 1/20 (distillation/reflux ratio) until the boiling point reached 81° C. Then the column was set at that total reflux. After heating for an additional 4 hours, the solution was cooled to room temperature. Five drops of triethylamine were added and solvent was removed by evaporation. The product was a viscous liquid having a weight average molecular weight (MW) of 29,000 as determined by GPC.

EXAMPLE 2

Following the procedure as described in Example 1, 52.878 g (0.30 mole) of triethylorthopropionate was reacted with 40.25 g (0.30 mole) of 1,2,6-hexanetriol. The by-product ethanol was removed by azeotropic distillation with cyclohexane to yield a polymer having a MW of 19,300.

EXAMPLE 3

Following the procedure as presented in Example 1, 14.82 g (0.10 mole) of trimethylorthobutyrate was reacted with 13.42 g (0.10 mole). The by-product methanol was removed by azeotropic distillation with cyclohexane from 54° C. to 81° C. to yield a polymer having a MW of 27,600.

EXAMPLE 4

Following the procedure as presented in Example 1, 16.223 g (0.10 mole) of triethylorthoacetate was reacted with 12.015 g (0.10 mole) of 1,2,5-pentanetriol to yield a polymer having a MW of 25,000.

EXAMPLE 5

A bioerodible ointment was prepared with 2 wt % hydrocortisone physically dispersed in a soft, bioerodible ortho ester polymer having the structure

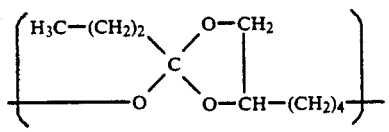

synthesized using the methods described in the preceding examples. To demonstrate bioerodibility, a body of this ointment was exposed to a slow (9 mm/min) flow of buffer solution, pH 7.4. Fractions were collected and the appearance of the drug in the collected buffer was analyzed by HPLC. Because hydrolysis of orthoester linkages at pH 7.4 is very slow, no hydrocortisone was released in the absence of an incorporated acidic excipient. Upon incorporation of 2 wt% of adipic acid into the bioerodible ointment, bioerosion took place and hydrocortisone was released. Results are summarized graphically in FIG. 1. The rate of hydrocortisone release can thus be controlled by the amount of the incorporated acidic excipient or the use of materials having varying acidity.

What is claimed is:

1. A method for preparing a bioerodible polymer comprising:
reacting a monomeric ortho ester having the general formula

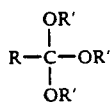

wherein R is hydrogen or alkyl of 1 to 10 carbon atoms and R' is lower alkyl with a triol having the general formula

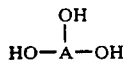

wherein A is selected from alkylenes and cycloalkylenes of at least 5 carbon atoms, and oxyalkylenes and cyclooxyalkylenes of at least 5 carbons, to form without isolation of any intermediate species a nonrigid, bioerodible ortho ester polymer comprising mer units of the structure

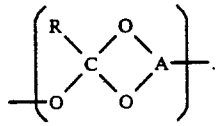

2. The method of claim 1 wherein R is hydrogen or lower alkyl.

3. The method of claim 1 wherein A is an alkylene of from about 5 to about 20 carbon atoms.

4. The method of claim 1 wherein A is a cycloalkylene moiety of from about 5 to 20 carbon atoms.

5. The method of claim 1 wherein A is a cyclooxyalkylene moiety of from about 5 to about 20 carbon atoms.

6. The method of claim 5 wherein said triol is a sugar residue.

7. The method of claim 1 wherein A has the general formula:

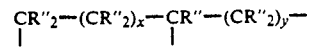

wherein x is 0 or 1, y is greater than or equal to 2, and the R"s are independently selected from the group consisting of hydrogen and lower alkyl.

8. The method of claim 7 wherein x is 0, y is 4 and the R"s are each hydrogen.

9. The method of claim 1 wherein the number of mer units in the final polymer is in the range of about 2 to about 1000.

10. A polymer containing repeating mer units of the structure

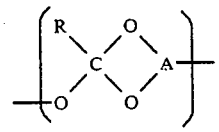

wherein R is hydrogen or alkyl of 1 to 10 carbon atoms and A is selected from the group consisting of cycloalkylenes and cyclooxyalkylene of at least 5 carbon atoms.

11. The polymer of claim 10 wherein A is a pentafuranose ring.

12. The polymer of claim 10 having a molecular weight of at least about 5,000.

13. The polymer of claim 10 having a molecular weight of at least about 20,000.

14. The polymer of claim 10 having a molecular weight of at least about 50,000.

15. A bioerodible pharmaceutical composition comprising in the form of an ointment an effective therapeutic amount of a therapeutic agent dispersed in a carrier comprising the polymer of claim 10 in combination with a pharmaceutically acceptable carrier.

16. The composition of claim 15 further comprising an added acidic excipient.

17. A method for treating deep wounds, comprising administering to an affected patient an effective amount of a composition of any one of claims 15, 16, or 20, in which the therapeutic agent is a deep wound treating agent.

18. A method for treating periodontal disease, comprising administering to an affected patient an effective amount of a composition of any one of claims 15, 16, or 20 in which the therapeutic agent is a periodontal disease treating agent.

19. The composition of any one of claims 15, 16 or 20 wherein said therapeutic agent is an antibacterial agent.

20. The composition of any one of claims 15, 16 or 20 wherein said therapeutic agent is an antibiotic.

21. The composition of any one of claims 15, 16, or 20 wherein said therapeutic agent is a proteinaceous drug.

22. The composition of claim 21 wherein said proteinaceous drug is an epidermal growth factor.

23. The composition of claim 21 wherein said proteinaceous drug is a growth hormone.

24. The composition of claim 15 wherein said therapeutic agent is hydrocortisone.

25. The method of claim 17 wherein said deep wound treating agent is a proteinaceous drug.

26. A bioerodible pharmaceutical composition comprising, in the form of an ointment, an effective therapeutic amount of a therapeutic agent dispersed in a carrier comprising a polymer containing repeating mer units of the structure

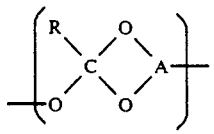

wherein R is hydrogen or alkyl of 1 to 10 carbon atoms and A is selected from the group consisting of cycloalkylenes of at least 5 carbon atoms, cyclooxyalkylenes of at least 5 carbon atoms, and alkylenes having the structure $CH_2-(CR''_2)_x-CR''-(CR''_2)_y-$, wherein x is 0 or 1, y is greater than or equal to 3, and R''s are independently selected from the group consisting of hydrogen and lower alkyl, and a pharmaceutically acceptable acidic excipient.

* * * * *